United States Patent
Tendler et al.

(10) Patent No.: US 9,475,838 B2
(45) Date of Patent: *Oct. 25, 2016

(54) PROCESS FOR PURIFICATION OF A FATTY ACID BINDING PROTEIN

(71) Applicants: Fundacao Oswaldo Cruz, Rio de Janeiro (BR); Ouro Fino Agronegocio Ltda., Cravinhos, Sao Paulo (BR)

(72) Inventors: Miriam Tendler, Rio de Janeiro (BR); Celso Raul Romero Ramos, Rio de Janeiro (BR); Andrew J. G. Simpson, New York, NY (US)

(73) Assignees: OURO FINO AGRONEGOCIO LTDA., Sao Paulo (BR); FUNDACAO OSWALDO CRUZ, Rio De Janeiro (BR)

(*) Notice: Subject to any disclaimer, the term of this patent is extended or adjusted under 35 U.S.C. 154(b) by 0 days.

This patent is subject to a terminal disclaimer.

(21) Appl. No.: 14/886,794

(22) Filed: Oct. 19, 2015

(65) Prior Publication Data

US 2016/0052963 A1    Feb. 25, 2016

Related U.S. Application Data

(62) Division of application No. 13/824,378, filed as application No. PCT/BR2011/000320 on Sep. 13, 2011, now Pat. No. 9,193,772.

(30) Foreign Application Priority Data

Sep. 17, 2010 (BR) ..................... 1005855

(51) Int. Cl.
| | |
|---|---|
| C07K 14/435 | (2006.01) |
| C07K 1/36 | (2006.01) |
| C12N 15/81 | (2006.01) |
| C07K 14/395 | (2006.01) |
| A61K 38/00 | (2006.01) |
| A61K 39/00 | (2006.01) |

(52) U.S. Cl.
CPC ............. *C07K 1/36* (2013.01); *C07K 14/395* (2013.01); *C07K 14/43559* (2013.01); *C12N 15/815* (2013.01); *A61K 38/00* (2013.01); *A61K 39/0003* (2013.01)

(58) Field of Classification Search
None
See application file for complete search history.

(56) References Cited

U.S. PATENT DOCUMENTS

2007/0021332 A1    1/2007    Tendler et al.

FOREIGN PATENT DOCUMENTS

WO    2004067698 A2    8/2004

OTHER PUBLICATIONS

Moser et al. "A 14-kDa Schistosoma mansoni Polypeptide Is Homologous to a Gene Family of Fatty Acid Binding Proteins" J. Biol. Chem., 1991, vol. 266, pp. 8447-8454.*
Li et al., "High level expression, purification, and characterization of the shrimp antimicrobial peptide, Ch-penaeidin, in Pichia pastoris", Protein Expression and Purification, vol. 39, pp. 144-151 (2005).
Becker et al., "Gene cloning, overproduction and purification of a functionally active cytoplasmic fatty acid-binding protein (Sj-FABPc) from the human blood fluke Schistosoma japonicum." Gene 148(2): 321-325 (1994).
Abstract of Brito et al., "Human IgG1 and IgG3 recognition of Schistosoma mansoni 14kDa fatty acid-binding recombinant protein." Parasite Immunology 22: 41-48 (2000).
Cregg et al., "Recent advances in the expression of foreign genes in Pichia pastoris." BioTechnology 11: 905-910 (1993).
Faber et al., "Review: Methylotrophic yeasts as factories for the production of foreign proteins." Yeast 11.14: 1331-1344 (1995).
Li et al., "Expression of recombinant proteins in Pichia pastoris." Applied biochemistry and biotechnology 142.2: 105-124 (2007).
Ramos et al., "r-Sm14-pRSETA efficacy in experimental animals." Memorias do Instituto Oswaldo Cruz 96, Suppl.: 131-135 (2001).
Ramos et al., "Stability improvement of the fatty acid binding protein Sm14 from S. mansoni by Cys replacement: structural and functional characterization of a vaccine candidate." Biochimica et Biophysica Acta (BBA)-Proteins and Proteomics 1794.4: 655-662 (2009).
Roymondal et al., "Predicting gene expression level from relative codon usage bias: an application to *Escherichia coli* genome." DNA research 16.1: 13-30 (2009).
Tendler et al., "A Schistosoma mansoni fatty acid-binding protein, Sm14, is the potential basis of a dual-purpose anti-helminth vaccine." Proceedings of the National Academy of Sciences 93.1: 269-273 (1996).
International Search Report for PCT/BR2011/000320 dated Dec. 26, 2011.

* cited by examiner

*Primary Examiner* — Christina Bradley
(74) *Attorney, Agent, or Firm* — Caesar Rivise, PC

(57) ABSTRACT

A process for purification of a fatty acid binding proteins such as, e.g., Sm14 of *Pichia pastoris* or type-3 FABP protein of *Fasciola hepatica*. The process includes the steps of: (a) performing lysis of cells containing the fatty acid binding protein to obtain a lysate; (b) clarifying the lysate obtained in step (a) to obtain a clarified lysate; (c) loading the clarified lysate in a column containing an anion exchange resin; (d) eluting proteins from the column by pH changes in the column; and (e) separating contaminant proteins from the fatty acid binding protein by gel-filtration.

7 Claims, 4 Drawing Sheets

SEQUENCE LISTING

```
<160> NUMBER OF SEQ ID NOS: 3

<210> SEQ ID NO 1
<211> LENGTH: 133
<212> TYPE: PRT
<213> ORGANISM: Schistosoma mansoni

<400> SEQUENCE: 1

Met Ser Ser Phe Leu Gly Lys Trp Lys Leu Ser Glu Ser His Asn Phe
1               5                   10                  15

Asp Ala Val Met Ser Lys Leu Gly Val Ser Trp Ala Thr Arg Gln Ile
                20                  25                  30

Gly Asn Thr Val Thr Pro Thr Val Thr Phe Thr Met Asp Gly Asp Lys
            35                  40                  45

Met Thr Met Leu Thr Glu Ser Thr Phe Lys Asn Leu Ser Val Thr Phe
        50                  55                  60

Lys Phe Gly Glu Glu Phe Asp Glu Lys Thr Ser Asp Gly Arg Asn Val
65                  70                  75                  80

Lys Ser Val Val Glu Lys Asn Ser Glu Ser Lys Leu Thr Gln Thr Gln
                85                  90                  95

Val Asp Pro Lys Asn Thr Thr Val Ile Val Arg Glu Val Asp Gly Asp
                100                 105                 110

Thr Met Lys Thr Thr Val Thr Val Gly Asp Val Thr Ala Ile Arg Asn
            115                 120                 125

Tyr Lys Arg Leu Ser
    130

<210> SEQ ID NO 2
<211> LENGTH: 402
<212> TYPE: DNA
<213> ORGANISM: Artificial Sequence
<220> FEATURE:
<223> OTHER INFORMATION: Synthetic sequence coding for Sm14 MV protein
```

```
<400> SEQUENCE: 2
atgtcttctt tcttgggtaa gtggaagttg tctgaatctc acaacttcga cgctgttatg      60
tctaagttgg gtgtttcttg ggctaccaga caaattggta acaccgttac tccaaccgtt     120
accttcacca tggacggtga caagatgact atgttgaccg agtctacctt caagaacttg     180
tctgttactt tcaagttcgg tgaagagttc gacgaaaaga cttctgacgg tagaaacgtt     240
aagtctgttg ttgaaaagaa ctctgaatct aagttgactc aaactcaagt tgacccaaag     300
aacactaccg ttatcgttag agaagttgac ggtgacacta tgaagactac tgttaccgtt     360
ggtgacgtta ccgctatcag aaactacaag agattgtctt aa                        402

<210> SEQ ID NO 3
<211> LENGTH: 419
<212> TYPE: DNA
<213> ORGANISM: Artificial Sequence
<220> FEATURE:
<223> OTHER INFORMATION: Synthetic gene for Sm14 protein with Kozak
      sequence and restriction sites

<400> SEQUENCE: 3
ggatccaaac gatgtcttct ttcttgggta agtggaagtt gtctgaatct cacaacttcg      60
acgctgttat gtctaagttg ggtgtttctt gggctaccag acaaattggt aacaccgtta     120
ctccaaccgt taccttcacc atggacggtg acaagatgac tatgttgacc gagtctacct     180
tcaagaactt gtctgttact ttcaagttcg gtgaagagtt cgacgaaaag acttctgacg     240
gtagaaacgt taagtctgtt gttgaaaaga actctgaatc taagttgact caaactcaag     300
ttgacccaaa gaacactacc gttatcgtta gagaagttga cggtgacact atgaagacta     360
ctgttaccgt tggtgacgtt accgctatca gaaactacaa gagattgtct taagaattc     419
```

PROCESS FOR PURIFICATION OF A FATTY ACID BINDING PROTEIN

SEQUENCE LISTING STATEMENT

Incorporated herein by reference in its entirety is a Sequence Listing file named "B120420024_SeqLst_20151019_ST25.txt", which was submitted to the USPTO via EFS-web on Oct. 19, 2015 as an ASCII text file 3 KB in size. This file, which was created Oct. 19, 2015, constitutes both the paper and computer readable form of the Sequence Listing.

FIELD OF APPLICATION

The present invention is related to the field of recombinant protein production using a synthetic gene associated with high protein expression in *Pichia pastoris*. More specifically, this invention describes the production of Sm14 *Schistosoma mansoni* recombinant protein. A synthetic gene was created to promote high Sm14 expression, and with this gene we obtained and genetically manipulated a *Pichia pastoris* strain for effectively producing a vaccine. We have also improved that protein's production and purification processes from *P. pastoris* cells; the industrial production of such processes may be scheduled.

INVENTION FUNDAMENTALS

The Sm14 protein's molecular weight is approximately 14.8 kDa and it is significantly similar to proteins that belong to the protein family which binds to fatty acids. It has been widely studied and described by applicant in his previous patent applications.

The three-dimensional structure of protein Sm14 was predicted through molecular modeling by computerized homology, as well as crystallography and Nuclear Magnetic Resonance. The structure of protein Sm14 allowed us to identify potential protective epitopes and enabled us to use rSm14 as a vaccination antigen.

Sm14's structure, as well as models built for homologous *Fasciola hepatica* proteins (FABP type 3 is the one with greater shared sequential identity, 49%), shows that those molecules adopt three-dimensional configurations that are similar to molecules of other protein families that bind to lipids (Fatty Acid Binding Proteins—FABP).

Therefore, based on the entire state of the art knowledge gathered by inventors, we will demonstrate here how Sm14 recombinant forms can provide significant protection against infections caused by supposedly pathogenic heltminths in relation to humans and animals.

In papers which demonstrated Sm14's protective activity for the first time, the corresponding recombinant protein was expressed with the pGEMEX-Sm14 vector as inclusion bodies. After bodies were isolated and washed, the protein was purified by preparative electrophoresis of the corresponding band (Tendler et al., 1996) by electroelution. However, this methodology was not adequate for producing proteins in a larger scale. Later, Sm14 started being produced with a fusion of six consecutive histidines (6×His) in the extreme amino-terminus of the *Escherichia coli* expression system, as inclusion bodies. After bodies were obtained and solubilized, refold was necessary in order to obtain a functional and immunologically active protein (Ramos et al., 2001).

Therefore, despite all the knowledge gathered by inventors, there are still disadvantages to be overcome in order to obtain antigenic material that may be obtained with high performance, at an industrial scale and under GMP conditions, and that will not lose its stability feature.

INVENTION SUMMARY

This invention proposes a platform for producing a recombinant vaccine against heltminths in *Pichia pastoris*. Through the abovementioned platform it is possible to obtain a recombinant vaccine against heltminths (in *P. pastoris*), including the production and purification processes of Sm14 developed in the *Pichia pastoris* system.

The invention also proposes a synthetic gene for Sm14 protein expression. *Pichia pastoris*' genetic transformation with this synthetic gene under control of the AOX1 promoter allows one to produce and purify Sm14.

Therefore, the invention allows us to obtain Sm14 from a synthetic gene containing codons optimized for high expression in *Pichia pastoris*, SEQ ID NO:3 (final gene sequence), as well as Sm14 purification procedures.

A BRIEF DESCRIPTION OF FIGURES

DETAILED DESCRIPTION OF THE INVENTION

Figure 1:
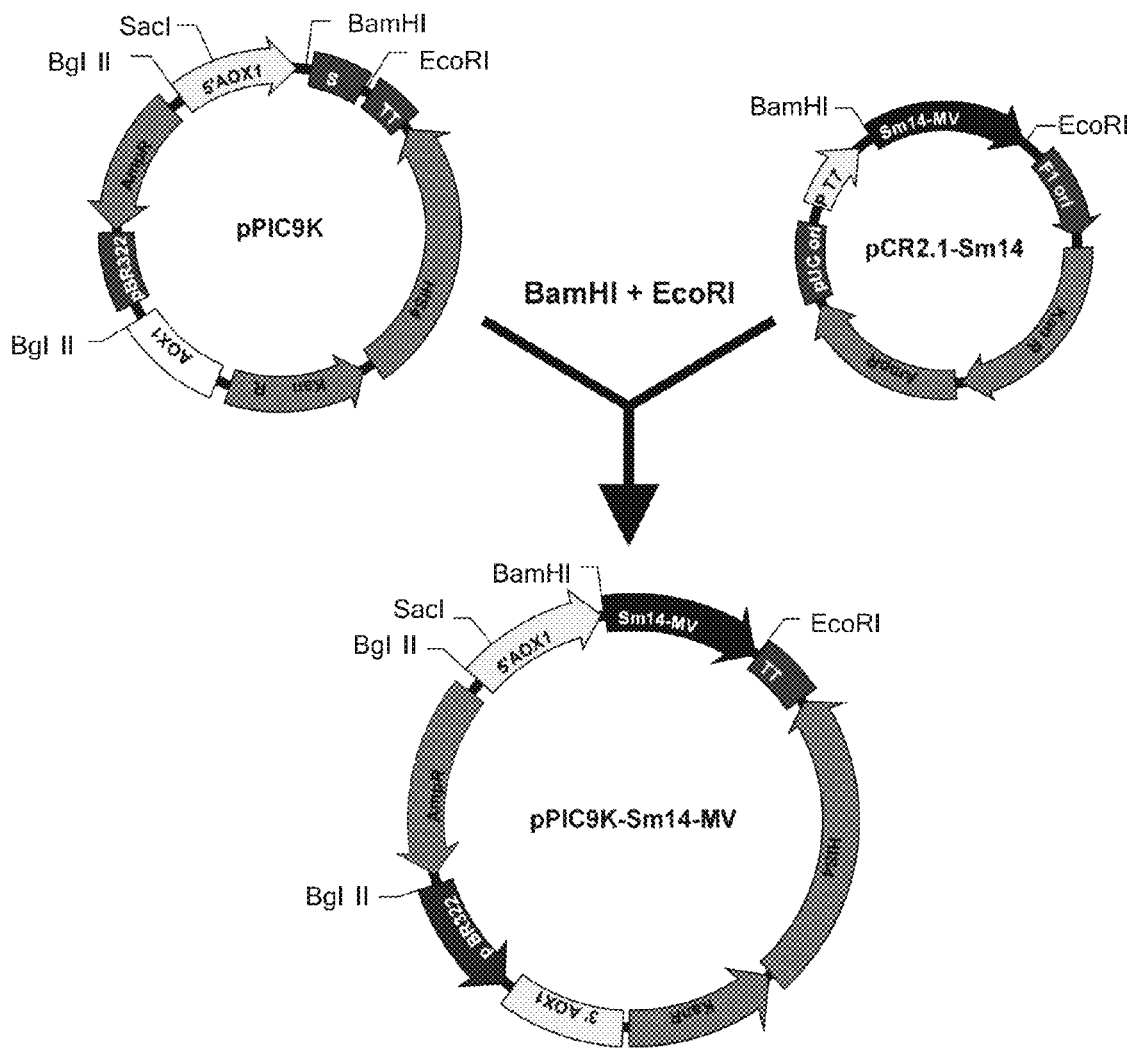
FIG. 1 shows the strategy for building the pPIC9K-Sm14-MV plasmid.

The main purpose of this invention is to produce a recombinant vaccine against heltminths. This goal can be achieved by producing recombinant proteins using a synthetic gene for high protein expression in *Pichia pastoris*. According to the invention a synthetic gene was created to promote high Sm14 expression, and with this gene we obtained a *Pichia pastoris* strain for effectively producing a vaccine. This invention also includes the protein's production and purification processes from *P. pastoris* cells; such processes may be scheduled for industrial production.

The expression system in methylotrophic yeast *Pichia pastoris* has significant advantages when compared with systems based on *E. coli* for producing recombinant proteins at an industrial scale. Among such advantages we can mention, for instance, the stability of transformed strains, high expression, high cell-density culture, easy culture scheduling, no human health hazards, and it does not produce endotoxins (Fabe et al., 1995). The latter advantage is one of the factors which influenced the change of microorganism for protein expression. This is because the need for detecting or quantifying endotoxins produced by Gram-negative bacteria in each batch would be a limiting factor, since products generated in *E. coli* that will later be used in human beings must be free from bacterial endotoxins. This additional requirement would make *E. coli* production processes difficult, and this would have a negative impact on final production costs.

The invention will now be described through its best execution process.

1. Obtaining the *Pichia Pastoris* Recombinant Strain 1.1 Synthetic Gene for Sm14 Expression in *P. pastoris:*

First a gene was designed and synthesized containing codons that were optimized to obtain maximum Sm14 expression in *P. pastoris*. In our case we used Sm14-MV; however any form of Sm14 can be used.

There is evidence in literature about differential use of codons between proteins with low and high expression levels in the same organism (Roymondal and Sahoo, 2009). However, codon usage tables available in databases (for example: www.kazusa.or.jp/codon) contain data from all body proteins, and do not take the level of gene expression into account. For this reason, in order to design the gene we initially drew up a codon usage table based on data about sequences that codify recombinant proteins expressed above 1 gram per culture Liter in *P. pastoris* (see Table 1), as well as the sequence for AOX1 protein (which represents 30% of total *P. pastoris* protein, after induction with methanol).

TABLE 1

List of high-expression recombinant proteins in *P. pastoris*.

| Expressed Protein | (mg/L) | Reference |
|---|---|---|
| Hydroxynitrile lyase | 22000 | Hasslacher, M. et al. (1997) Protein Expr. Purif. 11: 61-71 |
| Mouse gelatin | 14800 | Werten, M. W. et al. (1999) Yeast 15: 1087-1096 |
| Tetanus toxin fragment C | 12000 | Clare, J. J. et al. (1991) Bio/Technology 9: 455-460 |
| Human tumor necrosis factor | 10000 | Sreekrishna, K. et al. (1989) Biochemistry 28: 4117-4125 |
| α-amylase | 2500 | Paifer, E. et al. (1994) Yeast 10: 1415-1419 |
| T2A peroxidase | 2470 | Thomas, L. et al. (1998) Can. J. Microbiol. 44: 364-372 |
| Catalase L | 2300 | Calera, J. A. et al. (1997) Infect. Immun. 65: 4718-4724 |
| Hirudin | 1500 | Rosenfeld, S. A. et al. (1996) Protein Expr. Purif. 8: 476-482. |

For gene design we chose the sequence of Sm14-MV protein, which has a valine residue at position 62—replacing cystein, which makes it more stable (Ramos et al., 2009); it is represented here as SEQ ID NO:1.

```
                                              SEQ ID NO: 1
    MSSFLGKWKL SESHNFDAVM SKLGVSWATR QIGNTVTPTV

TFTMDGDKMT MLTESTFKNL SVTFKFGEEF DEKTSDGRNV

KSVVEKNSES KLTQTQVDPK NTTVIVREVD GDTMKTTVTV

GDVTAIRNYK RLS
```

After the first selection of codons according to the table drawn up with protein data from Table 1, we performed sequence depurations which resulted in donor transcription termination sites (ATTTA) and splicing cryptic receptors (MAGGTRAGT and YYYNTAGC, respectively) and repetitive sequences (cleavage sites for restriction enzymes BamHI and EcoRI). SEQ ID NO:2 shows the sequence designed to express Sm14-MV protein in *Pichia pastoris*.

```
                                              SEQ ID NO: 2
  1   ATGTCTTCTT TCTTGGGTAA GTGGAAGTTG TCTGAATCTC ACAACTTCGA

51   CGCTGTTATG TCTAAGTTGG GTGTTTCTTG GGCTACCAGA CAAATTGGTA

101   ACACCGTTAC TCCAACCGTT ACCTTCACCA TGGACGGTGA CAAGATGACT

151   ATGTTGACCG AGTCTACCTT CAAGAACTTG TCTGTTACTT TCAAGTTCGG

201   TGAAGAGTTC GACGAAAAGA CTTCTGACGG TAGAAACGTT AAGTCTGTTG

251   TTGAAAAGAA CTCTGAATCT AAGTTGACTC AAACTCAAGT TGACCCAAAG

301   AACACTACCG TTATCGTTAG AGAAGTTGAC GGTGACACTA TGAAGACTAC

351   TGTTACCGTT GGTGACGTTA CCGCTATCAG AAACTACAAG AGATTGTCTT

401   AA
```

We added the Kozak sequence of the AOX1 protein gene of *P. pastoris* (AAACG) to the 5"-end of the designed sequence. Finally, we added restriction sites for BamHI (GGATCC) and EcoRI (GAATTC) to 5' and 3'-ends of the designed gene, respectively.

SEQ ID NO:3 shows the final sequence of the synthetic gene for Sm14 protein production.

Figure 2:
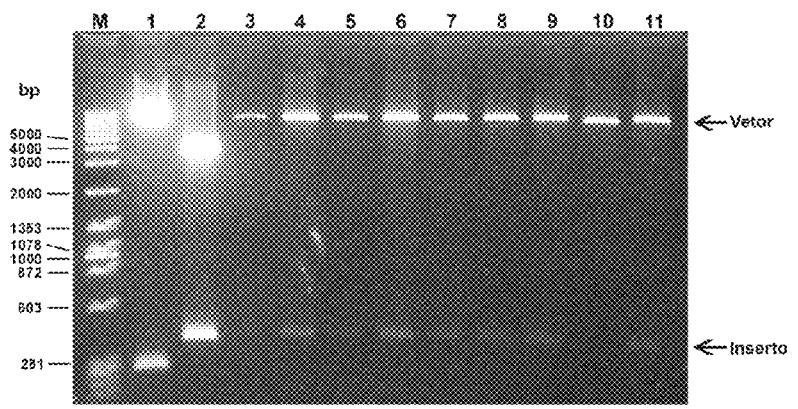
FIG. 2 shows the cloning of Sm14-MV into pPIC9K.

2. In FIG. 2 we show the results of Sm14-MV cloning in pPIC9K; clones were selected as shown below:

M.—1 Kb DNA ladder+phiX174/HaeIII
1.—pPIC9K/BamHI+EcoRI
2.—pCR21-Sm14-MV/BamHI+EcoRI
3 to 11.—Clones pPIC9K-Sm14-MV/BamHI+EcoRI.

```
                                                           SEQ ID NO: 3
  1    GGATCCAAAC GATGTCTTCT TTCTTGGGTA AGTGGAAGTT GTCTGAATCT

51    CACAACTTCG ACGCTGTTAT GTCTAAGTTG GGTGTTTCTT GGGCTACCAG

101    ACAAATTGGT AACACCGTTA CTCCAACCGT TACCTTCACC ATGGACGGTG

151    ACAAGATGAC TATGTTGACC GAGTCTACCT TCAAGAACTT GTCTGTTACT

201    TTCAAGTTCG GTGAAGAGTT CGACGAAAAG ACTTCTGACG GTAGAAACGT

251    TAAGTCTGTT GTTGAAAAGA ACTCTGAATC TAAGTTGACT CAAACTCAAG

301    TTGACCCAAA GAACACTACC GTTATCGTTA GAGAAGTTGA CGGTGACACT

351    ATGAAGACTA CTGTTACCGT TGGTGACGTT ACCGCTATCA GAAACTACAA

401    GAGATTGTCT TAAGAATTC
```

After synthesizing the designed sequence (SEQ ID NO:3), we performed cloning and later sequencing of the synthetic gene in vector pCR2.1 to confirm the synthesized sequence was faithful to the designed sequence.

1.2 Plasmid Construction for Sm14 Expression in *Pichia pastoris*:

The synthesized gene was cloned in vector pPIC9K where protein Sm14 is expressed without any fusion, making its intracellular production possible.

Vector pPIC9K (Invitrogen) was chosen for construction of the Sm14 expression plasmid in *P. pastoris* for the following reasons:

(1) It may be used to express intracellular proteins replacing the alpha-factor gene with the gene of choice, through the vector's BamHI restriction site, located before the Kozak sequence and the beginning of translation. In order to do this it was necessary to recreate the Kozak sequence before the ATG of the ORF to be expressed, according to the design of Sm14's synthetic gene.

(2) It offers the advantage of allowing a selection of clones with multiple copies integrated into the genome, by selecting resistance to antibiotic G418. There was no such possibility with pPIC9, used previously.

The strategy for building the pPIC9K-Sm14 plasmid is described in FIG. 1.

With plasmid pCR21-Sm14-MV, we changed the DH5α *E. coli* strain for its propagation. Afterward pDNA was purified with Qiaprep Spin Miniprep Kit (QIAGEN). This plasmid, as well as vector pPIC9K, was digested simultaneously with restriction enzymes BamHI and EcoRI (both of New England Biolabs). After digestion, DNA fragments were separated by agarose gel electrophoresis containing ethidium bromide. Fragments corresponding to vector pPIC9K and to the synthetic Sm14-MV insert were excised from the agarose gel and purified with a QIAquick Gel Extraction Kit (QIAGEN).

Purified fragments were linked using T4 DNA ligase (New England Biolabs). *E. coli*'s DH5α strain was transformed by the link reaction and clones were selected in LB agar medium containing ampicillin. The pDNA of a few ampicillin-resistant clones was purified and analyzed by restriction with enzymes BamHI and EcoRI, shown in FIG. 2. In FIG. 2 arrows mark the insert position and cloning vector.

Clones that showed bands corresponding to inserts were selected and sequenced with AOX5' primer to confirm successful cloning and the sequence's fidelity. Therefore, the synthetic sequence for Sm14 expression remained under control of strong alcohol oxidase 1 promoter (AOX1), which is induced by methanol (Cregg et al., 1993).

1.3 Transformation of *P. pastoris* with Plasmid pPIC9K-Sm14-MV and Selection of Recombinant Clones with Multiple Copies In order to produce the protein, the GS115 (his4) *P. pastoris* strain was transformed with plasmid pPIC9K-Sm14-MV. The latter was purified with the Maxiprep (Qiagen) kit. Plasmid DNA was digested separately with enzymes BglII and SacI (New England Biolabs), using 20 µg of DNA for each reaction. Digestion reactions were separated by agarose gel electrophoresis and bands with DNA fragments containing Sm14-MV's synthetic gene were severed from the gel and DNA was purified.

Electroporation-competent cells for the GS115 strain were prepared and transformed separately with purified DNA from restriction reactions for BglII and SacI (10 µg of DNA per transformation). Digestion with enzyme BglII guides the recombination of the expression cassette of AOX1's gene, in *P. pastoris* genome, while digestion with SacI can be integrated in other regions.

After transformation, cells were spread in to RD medium (histidine free medium, which contains: 1 M sorbitol; 2% dextrose; 1.34% YNB; $4 \times 10^{-5}$% biotine; and 0.005% of each amino acid: L-glutamate, L-methionine, L-lysine, L-leucine and L-isoleucine for selection of strains transformed by auxotrophy marker his4. Clones that managed to grow in the histidine-free medium were submitted to selection with antibiotic G418, at concentrations: 0.5; 1; 2; and 4 mg/ml, in a YPD culture (1% Yeast Extract, 2% Peptone; 2% dextrose) at 30° C. in microculture plates. Only clones transformed with plasmid pPIC9K-Sm14-MV digested with enzyme SacI managed to grow with G418 at 4 mg/ml; this characterizes the insertion of multiple copies of the expression cassette into *P. pistoris*' genome.

Figure 3:
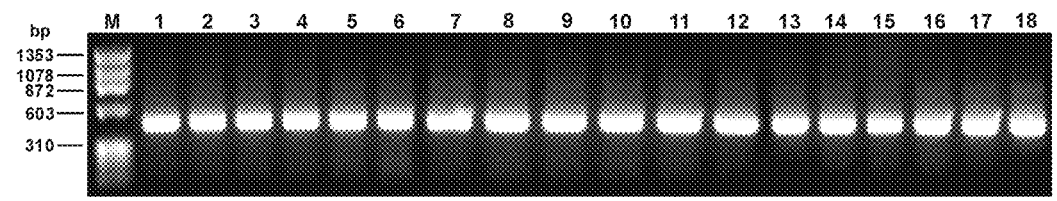
FIG. 3 shows the PCR analysis of *P. pastoris* clones.

In order to confirm whether selected clones had the expression cassette of the synthetic gene, genomic DNA of 17 clones was purified and used in PCR reactions with primers AOX5 and AOX3'. Plasmid pPIC9K-Sm14-MV was used as positive control. FIG. 3 shows the PCR analysis of P. pastoris GS115 clones transformed with pPIC9K-Sm14-MV and selected with 4 mg/ml of G418.

M.—phiX174/HaeIII
1 to 17.—Clones GS115/pPIC9K-Sm14-MV
18.—Positive control: plasmid pPIC9K-Sm14-MV.

As shown in FIG. 3, all clones selected with 4 mg/ml of G418 presented the sequence synthetic Sm14-MV.

Figure 4:
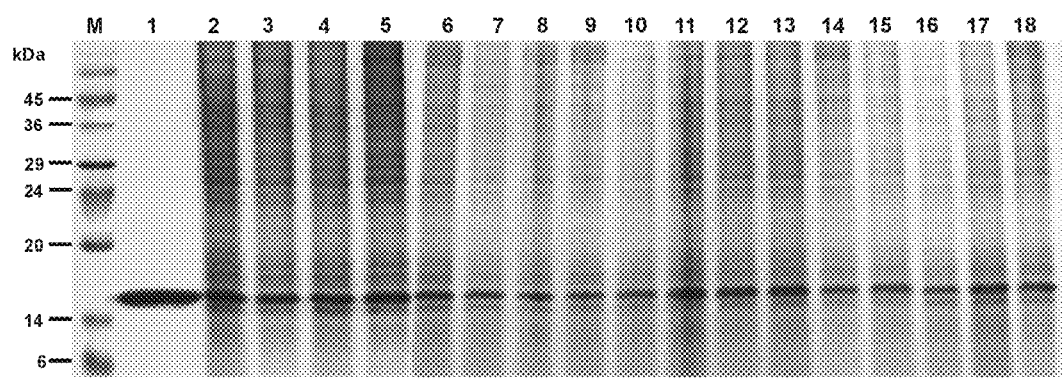
FIG. 4 shows the induction of Sm14 expression in *P. pastoris* clones GS115/pPIC9K-Sm14-MV.

In order to test the expression of Sm14 protein, clones grew in a BMG medium (Buffered Minimal Glycerol medium, containing: 1.34% YNB; 0.04% biotine, 0.1 M potassium phosphate pH 6.0; and 1% glycerol) for 48 hours and then were transferred to a BMM medium (Buffered Minimal Methanol medium, containing the same components as the BMG medium, except for glycerol which was replaced with 0.5% methanol and additional EDTA for the final concentration of 1 mM), for induction of expression of the recombinant protein. After 72 hours, adding 0.5% methanol every 24 hours, total proteins of each clone were analyzed by SDS-PAGE (FIG. 4). FIG. 4 shows the results of inducing the expression of Sm14 in P. pastoris clones GS115/pPIC9K-Sm14-MV.

M.—Low Molecular Weight Marker
1.—Positive control Sm14 purified fusionless E. coli protein
2 to 18—Total protein of clones 1-17 GS115/pPIC9K-Sm14-MV after induction with methanol.

Figure 5:
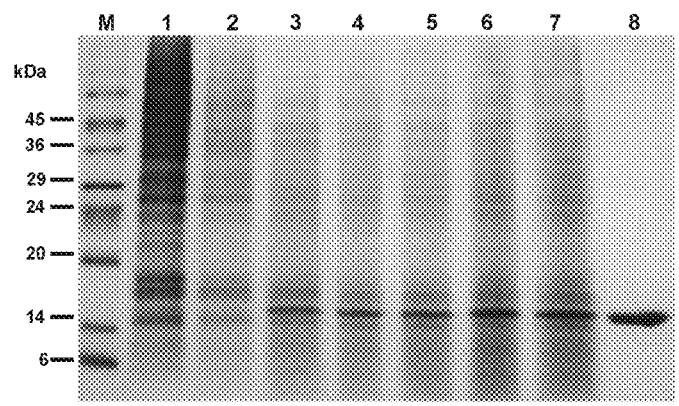
FIG. 5 shows the induction of Sm14 expression in *P. pastoris* GS115/pPIC9K-Sm14-MV.

1.4 Induction of Recombinant Sm14 Expression in P. pastoris GS115/pPIC9K-Sm14-MV FIG. 5 shows the induction of Sm14 expression in P. pastoris GS115/pPIC9K-Sm14-MV, where:
M.—Low Molecular Weight Marker
1.—Non-induced sample, in BMG medium
2 to 7.—Induction of expression for 0, 24, 48, 72 and 91 hours, respectively, in BMM medium
8.—Positive control Sm14 purified fusionless E. coli protein It was possible to observe a majority band in all selected clones which coincides with the size of purified E. coli purified fusionless Sm14 protein.

In order to confirm whether the protein was induced by methanol, clone #1 grew in a BMG medium for 48 hours (FIG. 5, lane 1) at 250 rpm, at 30° C.; it was later transferred to a BMM medium (0.5% methanol). We collected samples at different time intervals (FIG. 5, lanes 2 to 7). Methanol was added to the culture every 24 hours, to achieve a final concentration of 0.5%.

As FIG. 5 shows, in the BMG medium we did not obtain protein expression induced with methanol (FIG. 5, lane 1), and neither in time zero with BMM inducing medium (FIG. 5, lane 2). Induction was visible after 24 hours of culture in BMM medium and it remained stable during cell growth, until 91 hours which was the timeframe of the experiment.

Therefore, we have verified the specific induction of recombinant protein corresponding to Sm14 in P. pastoris.

In our experiment, by using only BMM medium and methanol at 0.5%, it was possible to achieve 26 grams of wet cell mass per liter of culture, maintaining a good level of expression of protein Sm14, which is cells' major protein after methanol induction. In addition to using a fermenter and more adequate means for producing recombinant proteins in P. pastoris, it is possible to obtain both greater cell mass and higher Sm14 expression.

2. Purification of Sm14 Recombinant Protein Expressed in P. Pastoris Strain GS115/pPIC9K-Sm14-MV The purification protocol for recombinant Sm14 from P. pastoris cytoplasm was based on methodology developed at the Experimental Schistosomiasis Laboratory of the Oswaldo Cruz Institute (IOC) for Sm14 purification without fusion into the E. coli system.

Lysis: Purification of recombinant proteins begins with lysis of P. pastoris cells. To that end, cells are resuspended 30 mM Tris-HCl 30 mM pH 9.5 and French press lysed. Lysate is clarified by centrifugation (FIG. 6, lane 2).

Capture:
Clarified lysate is loaded in resin Q-Sepharose XL (a quaternary amine in a matrix of cross-linked agarose with dextran surface extenders, available from GE Healthcare), balanced with buffer A (30 mM Tris-HCl pH 9.5). All Sm14 protein of lysate is absorbed by the resin, since there is no Sm14 protein in the material that is not absorbed in the resin (FIG. 6, lane 3). After the protein is loaded, the column is washed with buffer A. Protein is eluted with buffer B (30 mM Tris-HCl pH 8.0) in the AKTA-fplc system (GE Healthcare) (FIG. 6, lanes 4-6).

Polishing:
Eluted protein of resin Q-sepharose XL presents few contaminant proteins. In order to separate those proteins from Sm14 we used gel-filtration. To do so, fractions of the ion exchange chromatography containing Sm14 were gathered and concentrated in the Centriprep YM-10 membrane (Millipore) and the material was applied to a column containing Sephacryl S100 HR 26/60 (size exclusion media comprised of the anion exchange resin allyl dextran and N,N' methylene bisacrylamide, available from GE Healthcare) using PBS pH 7.4 as the mobile phase. The chromatographic peak (FIG. 6, lane 8) presented the same retention volume as fusionless proteins produced in E. coli (FIG. 7).

Figure 6:
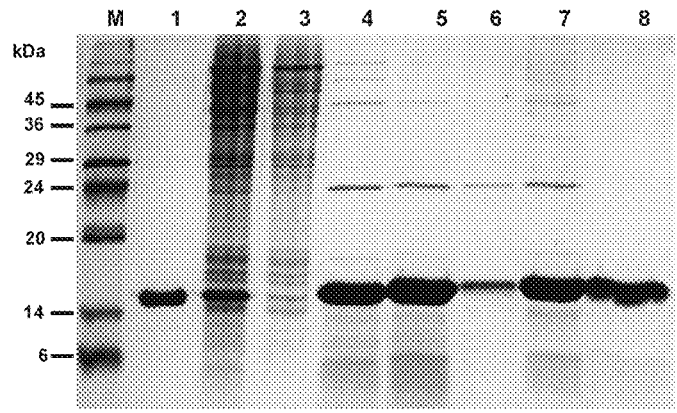
FIG. 6 shows the results of Sm14 purification.

FIG. 6 shows the results of Sm14 purification, where
M.—Low Molecular Weight Marker
1.—Positive control Sm14 purified fusionless E. coli protein
2.—Clarified lysate, 2.—Proteins not absorbed in resin Q-sepharose XL
3-6.—Resin Q-sepharose XL eluted fractions
7.—Pool of ion exchange chromatographic fractions
8.—Gel-filtration peak in column sephacryl S-100 HR 26/60

Figure 7:
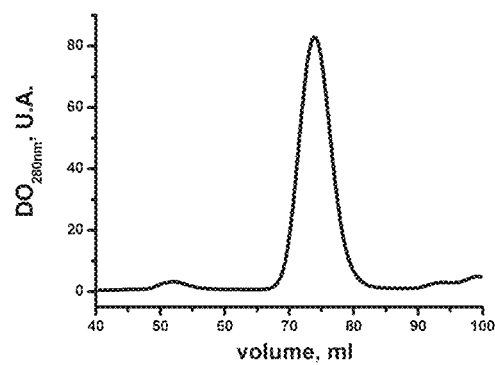
FIG. 7 shows the results of the gel-filtration chromatogram of the Sm14-MV protein produced in *P. pastoris*.

FIG. 7 shows the results of the gel-filtration chromatogram of the Sm14-MV protein produced in P. pastoris.

4—Analysis of Recombinant Sm14 Produced in Pichia pastoris

P. pastoris recombinant protein was purified using the same physical-chemical characteristics as the fusionless Sm14-MV protein expressed in E. coli. The purified protein of this form of P. pastoris corresponds in size to the protein specifically induced by methanol. Since we have the synthetic gene of Sm14-MV under control of AOX1 promoter in the expression cassette, we deduce that the expressed and purified P. pastoris protein is Sm14-MV.

Figure 8:
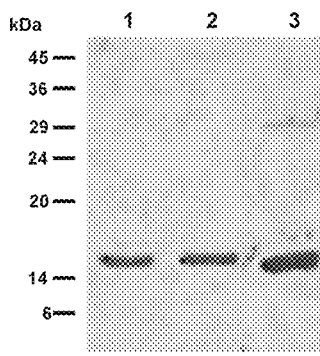
FIG. 8 shows a western blot analysis of the *P. pastoris* purified protein.

In order to confirm this statement, P. pastoris' purified protein was analyzed by western blot, using rabbit anti-Sm14 serum (FIG. 8). FIG. 8 represents the western blot analysis of P. pastoris' purified protein.

1 and 2.—P. pastoris' purified Sm14-MV protein
3.—Positive control Sm14 purified fusionless E. coli protein In this experiment we could observe that anti-Sm14 antibodies specifically recognized P. pastoris' purified protein (rabbit serum does not recognize endogenous P. pastoris proteins, data not shown), therefore confirming its identity.

Figure 9:
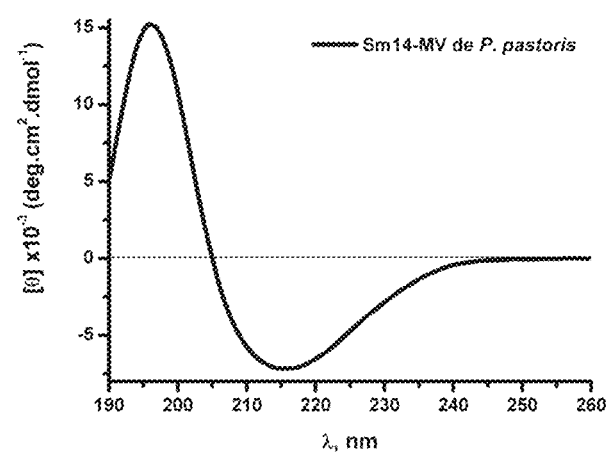
FIG. 9 shows the circular dichroism spectrum of the *P. pastoris* purified Sm14 protein.

Finally, it was necessary to identify whether the P. pastoris purified protein has a structure which corresponds to beta folding, which is typical of proteins of the Fatty Acid Binding Protein family, to which Sm14 belongs. To do so, protein samples were analyzed by circular dichroism, using spectral photopolarimeter J-815 (JASCO) (FIG. 9). FIG. 9 shows the circular dichroism spectrum of *P. pastoris*' purified Sm14 protein.

As one can see in FIG. 9, the spectrum corresponds to a beta-structure protein. This spectrum was similar to circular dichroism spectra of lots of *E. coli* Sm14 protein previously purified in the Experimental Schistosomiasis Laboratory.

Thus, based on the report above we may conclude that this invention will allow us to:

design and synthesize a synthetic gene for high expression of Sm14-MV in *Pichia pastoris*;

build a pPIC9K-Sm14-MV expression plasmid that contains the synthetic gene's sequence under control of AOX1 promoter;

obtain a *P. pastoris* strain that produces Sm14 and;

purify Sm14 in two chromatographic stages, whose scheduling for industrial production is feasible.

Therefore, the invention described herein shows that the Sm14 protein protects against infections caused by *Schistosoma mansoni* in mice, in platforms *E. coli* and *P. pastoris*.

REFERENCES (1) Cregg, J. M., Vedvick, T. S. and Raschke, W. C. Recent advances in the expression of foreign genes in *Pichia pastoris*. *BioTechnology* v. 11, p. 905-910, 1993.

(2) Faber, K. N., Harder, W., and Veenhuis, M. Review: Methylotropic Yeasts as Factories for the Production of Foreign Proteins. *Yeast*. v. 11, p. 1331-1344, 1995.

(3) Ramos, C. R., Spisni, A., Oyama, S. Jr., Sforca, M. L., Ramos, H. R, Vilar, M. M., Alves, A. C., Figueredo, R. C., Tendler, M., Zanchin, N. I., Pertinhez, T. A., Ho, P. L. Stability improvement of the fatty acid binding protein Sm14 from *S. mansoni* by Cys replacement: structural and functional characterization of a vaccine candidate. *Biochim Biophys Acta*. v. 1794, p. 655-662, 2009.

(4) Ramos, C. R., Vilar, M. M., Nascimento, A. L., Ho, P. L., Thaumaturgo, N., Edelenyi, R., Almeida, M., Dias, W. O., Diogo, C. M., Tendler, M. r-Sm14-pRSETA efficacy in experimental animals. *Mem Inst Oswaldo Cruz*. v. 96, p. 131-135, 2001.

(5) Roymondal, U. D. and Sahoo, S. S. Predicting gene expression level from relative codon usage bias: an application to *Escherichia coli* genome. *DNA Res*. v. 16, p. 13-30, 2009.

(6) Tendler, M., Brito, C. A., Vilar, M. M., Serra-Freire, N., Diogo, C. M., Almeida, M. S., Delbem, A. C., Da Silva, J. F., Savino, W., Garratt, R. C., Katz, N., Simpson, A. S. A *Schistosoma mansoni* fatty acid-binding protein, Sm14, is the potential basis of a dual-purpose anti-helminth vaccine. *Proc Natl Acad Sci USA*. v. 93, p. 269-273, 1996.

What is claimed is:

1. A process for purification of a recombinant Sm14 *Schistosoma mansoni* protein, said process comprising the steps of:
   (a) performing lysis of cells containing the Sm14 protein to obtain a lysate;
   (b) clarifying the lysate obtained in step (a) to obtain a clarified lysate;
   (c) loading the clarified lysate in a column containing an anion exchange resin;
   (d) eluting proteins from the column by pH changes in the column; and
   (e) separating contaminant proteins from the Sm14 protein by gel-filtration, wherein said Sm14 protein is encoded by SEQ ID NO:3 and is expressed in *Pichia pastoris*.

2. The process according to claim 1, wherein the lysis performing step comprises resuspending the cells in 30 mM Tris-HCl 30 mM pH 9.5 buffer and lysing the cells with a French press.

3. The process according to claim 2, wherein the clarifying step comprises centrifugation.

4. The process according to claim 3, wherein the loading step comprises loading the column with the clarified lysate in 30 mM Tris-HCl pH 9.5 buffer.

5. The process according to claim 4, wherein the eluting step comprises eluting the fatty acid binding protein from the column with 30 mM Tris-HCl pH 8.0 buffer.

6. The process according to claim 5, wherein the anion exchange resin comprises a quaternary amine in a matrix of cross-linked agarose with dextran surface extenders.

7. The process according to claim 6, wherein the separating step comprises gathering and concentrating eluted fractions from the eluting step, applying the eluted fractions to a gel filtration column containing size exclusion media comprised of the anion exchange resin allyl dextran and N,N'-methylene bisacrylamide, using phosphate buffered saline pH 7.4 as a mobile phase.

\* \* \* \* \*